United States Patent [19]

Guillen

[11] Patent Number: Plant 7,671

[45] Date of Patent: Oct. 8, 1991

[54] NEW GUINEA IMPATIENS PLANT NAMED CELEBRATION LIGHT LAVENDER

[75] Inventor: Mario A. Guillen, Cargato, Costa Rica

[73] Assignee: Ball Seed Co., West Chicago, Ill.

[21] Appl. No.: 531,577

[22] Filed: Jun. 1, 1990

[51] Int. Cl.[5] ..... A01H 5/00

[52] U.S. Cl. ..... Plt./68

[58] Field of Search ..... Plt./68

*Primary Examiner*—James R. Feyrer

*Attorney, Agent, or Firm*—Foley & Lardner

[57] ABSTRACT

A distinct New Guinea Impatiens plant named Celebration Light Lavender characterized by its iridescent lavender flower color, large flowers, uniform and compact habit, variegated leaves, floriferous habit, and excellent branching.

1 Drawing Sheet

The present invention relates to a new and distinctive cultivar of New Guinea Impatiens plant, botanically known as New Guinea Impatiens and known by the cultivar name Celebration Light Lavender. The new cultivar was developed by me through controlled breeding by crossing the cultivar identified as Linda Vista selection #148 with the cultivar identified as Linda Vista selection #560. Both cultivars are selections of Pan American Seed, Linda Vista, Costa Rica.

Asexual reproduction by terminal cuttings taken at West Chicago, Ill., has shown that the unique features of this new New Guinea Impatiens are stabilized and are reproduced true to type in successive propagations.

The following characteristics in combination distinguish the new impatiens from other impatiens cultivars of this type known and used in the floriculture industry.

1. Intense lavender flower color.
2. Uniform and compact habit.
3. Floriferous habit, with numerous breaks and freely flowering.
4. Large flowers.
5. Variegated foliage.
6. Flowers are positioned above the foliage in uniform display.

The new cultivar can be compared in flower color to the impatiens cultivar Comet, disclosed in U.S. Plant Pat. No. 5,920, although the lavender flower color of Celebration Light Lavender is somewhat darker and more intense. Reference is made to attached Chart A which notes dissimilar characteristics between the respective cultivars. To summarize, compared to Comet, Celebration Light Lavender has a more uniform and compact habit, flowers which are held above the foliage in a uniform display, more freely flowering, more breaks per plant, a different foliage variegation pattern, and slightly larger flowers.

The accompanying colored photograph illustrates the overall appearance of this cultivar, showing colors as true as it is reasonably possible to obtain in a colored reproduction of this type.

The following is a detailed description of my new New Guinea Impatiens cultivar based on plants produced under commercial practice in West Chicago, Ill., in a glass-covered greenhouse with day temperatures of 24° to 26° C. and night temperatures of 18° to 20° C.

Color references are made to The Royal Horticultural Society Colour Chart except where general terms of ordinary dictionary significance are used.

Propagation:

A. *Type cutting.*—Terminal tip.

B. *Time to initiate roots.*—5 days at 24° C. summer; 7 days at 21° C. winter.

C. *Rooting habit.*—Fibrous, branching.

Plant description:

A. *Form.*—Freely branching, vigorous.

B. *Habit of growth.*—Spreading, upright but compact habit, 22 cm. by 24 cm.; asymmetrical C. *Foliage.*—1. Size: 7.5 to 8.5 cm. in length, 4 cm. wide. 2. Shape: Ovate, acuminate tip with attenuate base. 3. Texture: Smooth. 4. Margin: Finely serrated. 5. Color: Green with yellow variegation. Young foliage: Top side 137A; under side 137B. Mature foliage: Top side 137A; under side 138B. 6. Variegation: 3B. 7. Venation: 55C.

Flowering description:

A. *Flowering habits.*—Freely flowering.

B. *Natural flowering season.*—Year-round in greenhouse environment.

C. *Flower bud shape and color.*—Conical, 143B.

D. *Flowers borne.*—Above foliage, arising from leaf axils.

E. *Quantity of flowers.*—8 to 10 per branch.

F. *Petals.*—1. Shape: Cordate. 2. Color: Lavender with white eye, iridescent. Top side, 77B when opening, 77B at maturity, fading to 75A. Under side 75B. 3. Number of petals: 5. 4. Size of flowers: 5 cm. (width)×5.5 cm. (length).

G. *Reproductive organs.*—1. Stamens: 5 in number. a. Anther shape: Oblong. b. Anther color: 10D. c. Pollen color: 11C. 2. Pistils: a. Stigma shape: Round. b. Stigma color: 154D. c. Style color: 143A. d. Ovary number: Superior, 5-celled. e. Ovary size: 0.75 cm. (length). f. Ovary color: 143C.

Disease resistance: No fungal or bacterial problems observed.

CHART A

| Characteristic | Celebration Light Lavender | Comet |
|---|---|---|
| Plant height | 7.5 cm. | 9 cm. |
| Plant diameter | 22 cm. by 24 cm; asyrommetrical | 14–20 cm. |
| Branches/plant | 6 | 4 |
| Foliage color | | |

CHART A-continued

| Characteristic | Celebration Light Lavender | Comet |
|---|---|---|
| Top side | 137A, variegated with 3B | 137A, variegated with 154A |
| Flower color | | |

CHART A-continued

| Characteristic | Celebration Light Lavender | Comet |
|---|---|---|
| Top side | 77B | 81C |
| Flower size | 5.5 cm. × 5 cm. | 5 cm. × 4.5 cm. |

I claim:

1. A new and distinct cultivar of New Guinea Impatiens plant named Celebration Light Lavender, as illustrated and described.

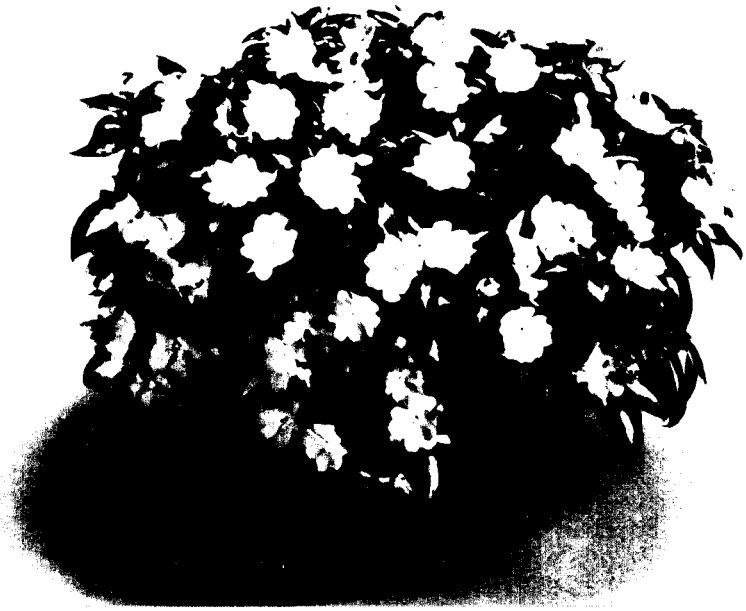

* * * * *